(12) United States Patent
Hall et al.

(10) Patent No.: US 11,723,762 B2
(45) Date of Patent: Aug. 15, 2023

(54) LIDAR BASED 3-D IMAGING WITH FAR-FIELD ILLUMINATION OVERLAP

(71) Applicant: Velodyne Lidar, Inc., Morgan Hill, CA (US)

(72) Inventors: David S. Hall, Los Altos Hills, CA (US); Mathew Noel Rekow, Santa Cruz, CA (US); Pieter J. Kerstens, Gilroy, CA (US)

(73) Assignee: VELODYNE LIDAR, INC., San Jose, CA (US)

( * ) Notice: Subject to any disclaimer, the term of this patent is extended or adjusted under 35 U.S.C. 154(b) by 0 days.

(21) Appl. No.: 15/420,366

(22) Filed: Jan. 31, 2017

(65) Prior Publication Data

US 2018/0164408 A1 Jun. 14, 2018

Related U.S. Application Data

(60) Provisional application No. 62/289,278, filed on Jan. 31, 2016.

(51) Int. Cl.
*G01S 7/48* (2006.01)
*A61C 19/06* (2006.01)
(Continued)

(52) U.S. Cl.
CPC .......... *A61C 19/063* (2013.01); *A61K 9/0053* (2013.01); *A61K 31/025* (2013.01);
(Continued)

(58) Field of Classification Search
None
See application file for complete search history.

(56) References Cited

U.S. PATENT DOCUMENTS 6,323,949 B1 * 11/2001 Lading .................... G01P 3/366
356/28.5
6,654,399 B1  11/2003 Kimura et al.
(Continued)

FOREIGN PATENT DOCUMENTS

CN      102736084 A     10/2012
CN      103608696 A      2/2014
(Continued)

OTHER PUBLICATIONS

Nejad, Unified Pulsed Laser Range Finder and Velocimeter using Ultra-Fast Time-To-Digital Converter, Iranian Journal of Electrical & Electronic Engineering, vol. 5, No. 2, Jun. 2009 (Year: 2009).*
(Continued)

*Primary Examiner* — Hovhannes Baghdasaryan
(74) *Attorney, Agent, or Firm* — Goodwin Procter LLP (57) ABSTRACT

Methods and systems for performing 3-D LIDAR measurements of objects simultaneously illuminated by two or more beams of light in the far field are described herein. A 3-D LIDAR based measurement device simultaneously emits at least two beams of light into a three dimensional environment from different locations. A portion of the three dimensional environment is simultaneously illuminated by the two or more light beams at a distance of at least five meters from the LIDAR device. However, the two or more light beams do not overlap at a distance less than five meters from the LIDAR device. The beams of light are slightly divergent, having highest intensity at the device and steadily lower intensity further away. By overlapping illumination beams in the far field, but not near the LIDAR device, overall intensity is maintained at moderate levels throughout the field of view of the LIDAR device.

23 Claims, 10 Drawing Sheets

(51) Int. Cl.
| | | |
|---|---|---|
| *G01S 7/481* | (2006.01) | |
| *G01S 7/487* | (2006.01) | |
| *G01S 17/89* | (2020.01) | |
| *G01S 17/10* | (2020.01) | |
| *G01C 3/08* | (2006.01) | |
| *G01S 17/931* | (2020.01) | |
| *A61P 1/02* | (2006.01) | |
| *A61K 9/00* | (2006.01) | |
| *A61K 31/025* | (2006.01) | |
| *A61K 31/075* | (2006.01) | |
| *A61K 31/164* | (2006.01) | |
| *A61K 31/198* | (2006.01) | |
| *A61K 31/205* | (2006.01) | |
| *A61K 31/355* | (2006.01) | |
| *A61K 31/714* | (2006.01) | |
| *A61K 31/728* | (2006.01) | |
| *A61K 36/28* | (2006.01) | |
| *A61K 36/48* | (2006.01) | |
| *A61K 36/52* | (2006.01) | |
| *A61K 36/63* | (2006.01) | |
| *A61K 36/736* | (2006.01) | |
| *A61K 36/752* | (2006.01) | |
| *A61K 36/81* | (2006.01) | |

(52) U.S. Cl.
CPC .......... *A61K 31/075* (2013.01); *A61K 31/164* (2013.01); *A61K 31/198* (2013.01); *A61K 31/205* (2013.01); *A61K 31/355* (2013.01); *A61K 31/714* (2013.01); *A61K 31/728* (2013.01); *A61K 36/28* (2013.01); *A61K 36/48* (2013.01); *A61K 36/52* (2013.01); *A61K 36/63* (2013.01); *A61K 36/736* (2013.01); *A61K 36/752* (2013.01); *A61K 36/81* (2013.01); *A61P 1/02* (2018.01); *G01C 3/08* (2013.01); *G01S 7/487* (2013.01); *G01S 7/4811* (2013.01); *G01S 7/4815* (2013.01); *G01S 7/4817* (2013.01); *G01S 17/10* (2013.01); *G01S 17/89* (2013.01); *G01S 17/931* (2020.01)

(56) References Cited

U.S. PATENT DOCUMENTS

| | | |
|---|---|---|
| 7,969,558 B2 | 6/2011 | Hall |
| 8,675,181 B2 | 3/2014 | Hall |
| 8,767,190 B2 | 7/2014 | Hall |
| 2009/0244515 A1 | 10/2009 | Behringer et al. |
| 2010/0020306 A1 | 1/2010 | Hall |
| 2010/0046953 A1 | 2/2010 | Shaw et al. |
| 2011/0216304 A1* | 9/2011 | Hall ........................ G01S 17/89 356/4.01 |
| 2012/0038903 A1 | 2/2012 | Weimer et al. |
| 2012/0256764 A1* | 10/2012 | Zeng ................... G01B 11/002 340/905 |
| 2014/0071234 A1 | 3/2014 | Millett |
| 2015/0015895 A1 | 1/2015 | Bridges et al. |
| 2015/0131080 A1 | 5/2015 | Retterath et al. |
| 2016/0041266 A1* | 2/2016 | Smits ...................... G01S 7/497 356/5.01 |

FOREIGN PATENT DOCUMENTS

| | | | |
|---|---|---|---|
| CN | 204989469 U | 1/2016 | |
| EP | 1584519 A1 * | 10/2005 | ........... G01S 17/931 |
| JP | H02-062087 A | 3/1990 | |
| JP | H04-061085 A | 2/1992 | |
| JP | H04-372891 A | 12/1992 | |
| JP | 2000-310679 A | 11/2000 | |
| JP | 2015-203697 A | 11/2015 | |

OTHER PUBLICATIONS

Canadian Patent Office, Office Action, App. No. 3,012,691 (dated Aug. 28, 2019), 4 pages.
Canadian Patent Office, Office Action, App. No. 3,012,691 (dated Jul. 16, 2021), 5 pages.
Canadian Patent Office, Office Action, App. No. 3,012,691 (dated Oct. 13, 2020), 4 pages.
European Patent Office, European Search Report, Appl. No. 17745113.5 (dated Jul. 26, 2021), 6 pages.
European Patent Office, European Search Report, Appl. No. 17745113.5 (dated Sep. 3, 2019), 8 pages.
International Search Report and Written Opinion of PCT/US2017/015874 dated May 23, 2017, 12 pages.
Japanese Patent Office, Office Action, App. No. 2018-539927 (dated May 25, 2021), 4 pages.
Japanese Patent Office, Office Action, App. No. 2018-539927 (dated Oct. 27, 2020), 4 pages.
Chinese Patent Office, CN Application No. 201780009103.6 Office Action dated Jan. 9, 2023, 11 pages.

* cited by examiner

LIDAR BASED 3-D IMAGING WITH FAR-FIELD ILLUMINATION OVERLAP

CROSS REFERENCE TO RELATED APPLICATION

The present application for patent claims priority under 35 U.S.C. § 119 from U.S. provisional patent application Ser. No. 62/289,278, entitled "LIDAR Based 3-D Imaging With Far-Field Illumination Overlap," filed Jan. 31, 2016, the subject matter of which is incorporated herein by reference in its entirety.

TECHNICAL FIELD

The described embodiments relate to LIDAR based 3-D point cloud measuring systems.

BACKGROUND INFORMATION

LIDAR systems employ pulses of light to measure distance to an object based on the time of flight (TOF) of each pulse of light. A pulse of light emitted from a light source of a LIDAR system interacts with a distal object. A portion of the light reflects from the object and returns to a detector of the LIDAR system. Based on the time elapsed between emission of the pulse of light and detection of the returned pulse of light, a distance is estimated. In some examples, pulses of light are generated by a laser emitter. The light pulses are focused through a lens or lens assembly. The time it takes for a pulse of laser light to return to a detector mounted near the emitter is measured. A distance is derived from the time measurement with high accuracy.

Some LIDAR systems employ a single laser emitter/detector combination combined with a rotating mirror to effectively scan across a plane. Distance measurements performed by such a system are effectively two dimensional (i.e., planar), and the captured distance points are rendered as a 2-D (i.e. single plane) point cloud. In some examples, rotating mirrors are rotated at very fast speeds (e.g., thousands of revolutions per minute).

In many operational scenarios, a 3-D point cloud is required. A number of schemes have been employed to interrogate the surrounding environment in three dimensions. In some examples, a 2-D instrument is actuated up and down and/or back and forth, often on a gimbal. This is commonly known within the art as "winking" or "nodding" the sensor. Thus, a single beam LIDAR unit can be employed to capture an entire 3-D array of distance points, albeit one point at a time. In a related example, a prism is employed to "divide" the laser pulse into multiple layers, each having a slightly different vertical angle. This simulates the nodding effect described above, but without actuation of the sensor itself.

In all the above examples, the light path of a single laser emitter/detector combination is somehow altered to achieve a broader field of view than a single sensor. The number of pixels such devices can generate per unit time is inherently limited due limitations on the pulse repetition rate of a single laser. Any alteration of the beam path, whether it is by mirror, prism, or actuation of the device that achieves a larger coverage area comes at a cost of decreased point cloud density.

As noted above, 3-D point cloud systems exist in several configurations. However, in many applications it is necessary to generate image information over a broad field of view. For example, in an autonomous vehicle application, the vertical field of view should extend down as close as possible to see the ground in front of the vehicle. In addition, the vertical field of view should extend above the horizon, in the event the car enters a dip in the road. In addition, it is necessary to have a minimum of delay between the actions happening in the real world and the imaging of those actions. In some examples, it is desirable to provide a complete image update at least five times per second. To address these requirements, a 3-D LIDAR system has been developed that includes an array of multiple laser emitters and detectors. This system is described in U.S. Pat. No. 7,969,558 issued on Jun. 28, 2011, the subject matter of which is incorporated herein by reference in its entirety.

In many applications, a sequence of pulses is emitted. The direction of each pulse is sequentially varied in rapid succession. In these examples, a distance measurement associated with each individual pulse can be considered a pixel, and a collection of pixels emitted and captured in rapid succession (i.e., "point cloud") can be rendered as an image or analyzed for other reasons (e.g., detecting obstacles). In some examples, viewing software is employed to render the resulting point clouds as images that appear three dimensional to a user. Different schemes can be used to depict the distance measurements as 3-D images that appear as if they were captured by a live action camera.

In some examples, the timing of successive light emission pulses is set such that the return signal associated with a particular pulse emission is detected before the subsequent pulse emission is triggered. This ensures that a detected return signal is properly associated with the particular pulse emission that generated the detected return signal.

In some other examples, multiple pulses are emitted into the surrounding environment before a return signal from any of the multiple pulses is detected. Traditionally, this approach raises the potential for cross-talk among detected signals. In other words, when multiple pulses are emitted into the surrounding environment before a return signal from any of the multiple pulses is detected, a detected return signal might be incorrectly associated with a different pulse emission than the particular pulse emission that gave rise to detected return signal. This can potentially cause errors in distance measurement.

Traditionally, to avoid cross-talk among multiple pulses, each of the multiple pulses is projected in a different direction. By projecting each of the multiple pulses in a different direction, each volume of space interrogated by each of the multiple pulses is completely separated from any volume of space interrogated by any of the other multiple pulses. As the separation among simultaneously interrogated spaces is increased, the likelihood of inducing measurement error due to cross-talk is reduced.

Existing LIDAR systems employ a single beam of light to interrogate a particular volume of the surrounding environment at any given time. The detection of return signals includes significant sources of measurement noise. These problems are exacerbated as measurement ranges are extended for a LIDAR system without increasing laser pulse intensity.

These systems are limited in the intensity of light that can be projected onto the volume of the environment subject to measurement by each beam of light. In some examples, human eye safety protocols limit the intensity of light emitted from the LIDAR device.

Improvements in signal strength and noise rejection are desired to extend the measurement range of a LIDAR system.

SUMMARY

Methods and systems for performing 3-D LIDAR measurements of objects simultaneously illuminated by two or more beams of light in the far field are described herein. A 3-D LIDAR based measurement device simultaneously emits at least two beams of light into a three dimensional environment. Each beam of light is emitted from the 3-D LIDAR device at a different location. At least two of the emitted beams are projected from the 3-D LIDAR device such that a portion of the three dimensional environment is illuminated by the two or more light beams at a distance of at least five meters from the LIDAR device. In addition, the two or more light beams do not overlap at a distance of less than five meters from the LIDAR device.

The beams of light emitted from the 3-D LIDAR device are slightly divergent. Thus, the beam intensity is highest at the window of the device, and steadily decreases further away from the device. It follows that the risk of damage to the human eye is greatest in short range of the device and the risk diminishes as the distance from the device increases.

By emitting multiple beams of light from the 3-D LIDAR device at different locations, the risk of eye damage is minimized at short distances because the beams are not overlapping. Hence, at short distances, only a single beam may incidentally interact with a human eye. As the distances increase, the beams begin to overlap, until a critical distance is reached where, ideally, two or more beams fully overlap with each other. In some examples, the critical distance is in a range of 100-200 meters away from the 3-D LIDAR device. At these distances, more than one beam may incidentally interact with a human eye without risk of harm due to beam divergence.

In a further aspect, the LIDAR system determines the time of flight of the multiple beams of illumination light projected from the LIDAR device to a location in three dimensional environment and back to the LIDAR device. The distance between the LIDAR device and the particular location of the three dimensional environment illuminated by the beams of illumination light is determined based on the time of flight.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Figure 1:
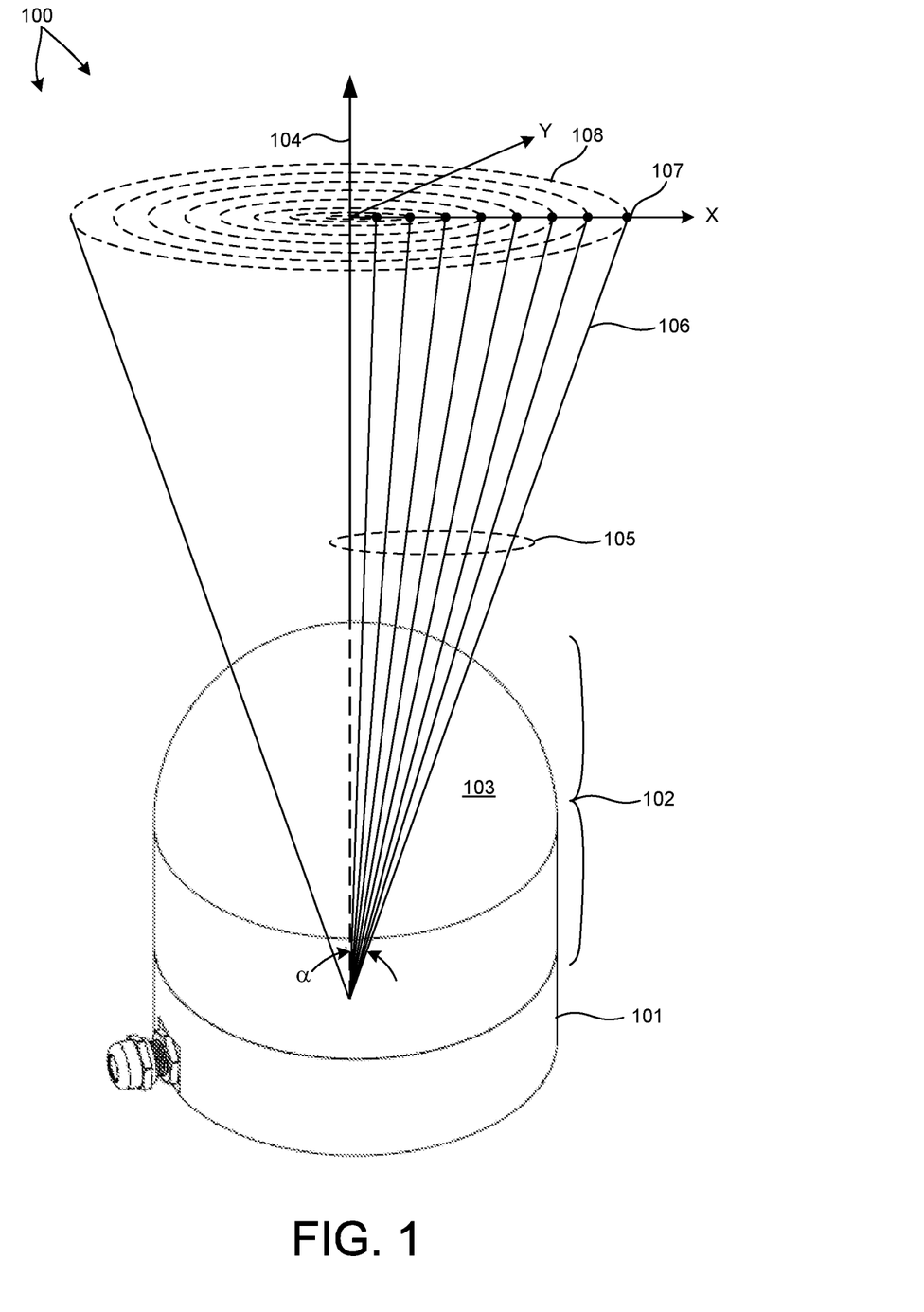
FIG. 1 is a simplified diagram illustrative of one embodiment of a 3-D LIDAR system 100 in at least one novel aspect.

FIG. 1 is a diagram illustrative of an embodiment of a 3-D LIDAR system 100 in one exemplary operational scenario. 3-D LIDAR system 100 includes a lower housing 101 and an upper housing 102 that includes a domed shell element 103 constructed from a material that is transparent to infrared light (e.g., light having a wavelength within the spectral range of 700 to 1,700 nanometers). In one example, domed shell element 103 is transparent to light having a wavelengths centered at 905 nanometers.

As depicted in FIG. 1, a plurality of beams of light 105 are emitted from 3-D LIDAR system 100 through domed shell element 103 over an angular range, a, measured from a central axis 104. In the embodiment depicted in FIG. 1, each beam of light is projected onto a plane defined by the x and y axes at a plurality of different locations spaced apart from one another. For example, beam 106 is projected onto the xy plane at location 107.

In the embodiment depicted in FIG. 1, 3-D LIDAR system 100 is configured to scan each of the plurality of beams of light 105 about central axis 104. Each beam of light projected onto the xy plane traces a circular pattern centered about the intersection point of the central axis 104 and the xy plane. For example, over time, beam 106 projected onto the xy plane traces out a circular trajectory 108 centered about central axis 104.

Figure 2:
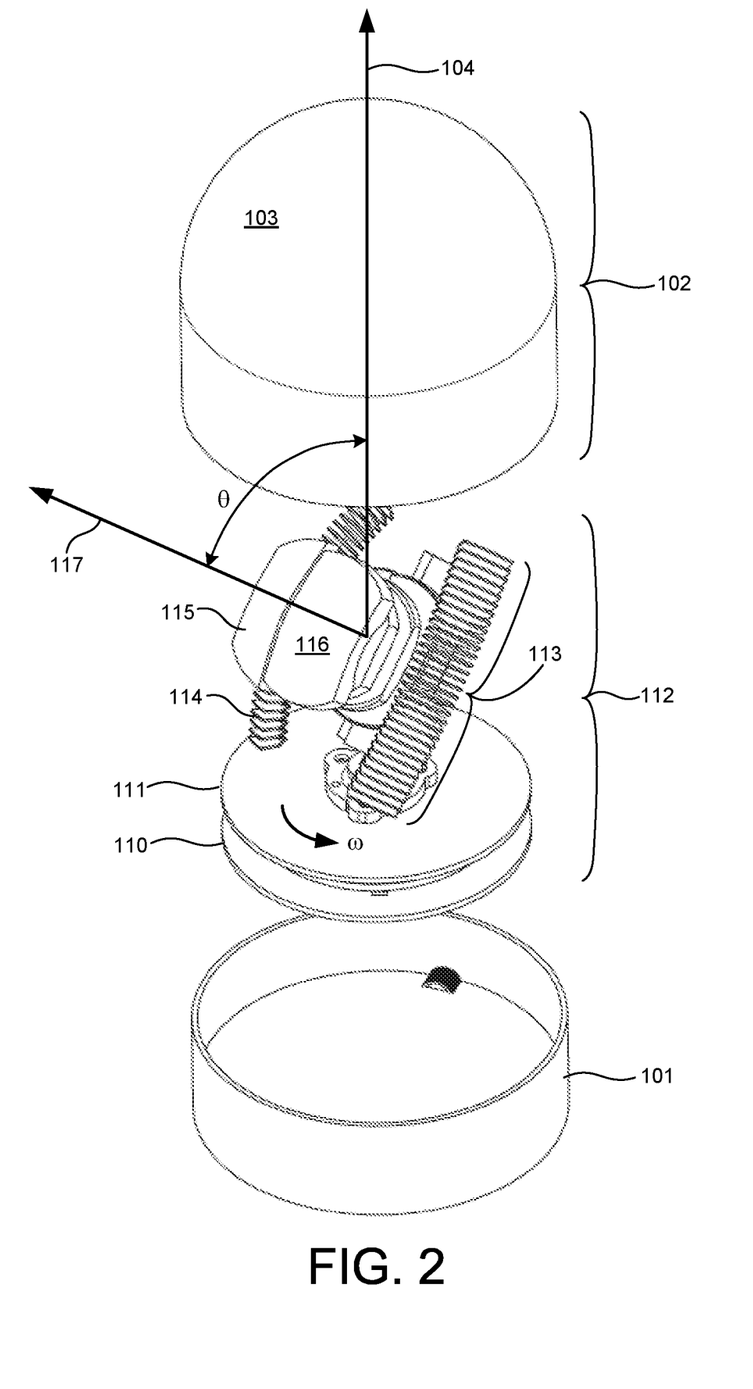
FIG. 2 depicts an exploded view of 3-D LIDAR system 100 in one exemplary embodiment.

FIG. 2 depicts an exploded view of 3-D LIDAR system 100 in one exemplary embodiment. 3-D LIDAR system 100 further includes a light emission/collection engine 112 that rotates about central axis 104. In the depicted embodiment, a central optical axis 117 of light emission/collection engine 112 is tilted at an angle, θ, with respect to central axis 104. As depicted in FIG. 2, 3-D LIDAR system 100 includes a stationary electronics board 110 mounted in a fixed position with respect to lower housing 101. Rotating electronics board 111 is disposed above stationary electronics board 110 and is configured to rotate with respect to stationary electronics board 110 at a predetermined rotational velocity (e.g., more than 200 revolutions per minute). Electrical power signals and electronic signals are communicated between stationary electronics board 110 and rotating electronics board 111 over one or more transformer, capacitive, or optical elements, resulting in a contactless transmission of these signals. Light emission/collection engine 112 is fixedly positioned with respect to the rotating electronics board 111, and thus rotates about central axis 104 at the predetermined angular velocity, ω.

As depicted in FIG. 2, light emission/collection engine 112 includes an array of light emitting elements 114 and an array of light detecting elements 113. Light emitted from each of the light emitting elements 114 is directed toward a mirror (not shown). Light reflected from the mirror passes through a series of illumination optics 115 that collimate the emitted light into an array of beams of light 105 that are emitted from 3-D LIDAR system 100 as depicted in FIG. 1. In general, any number of light emitting elements can be arranged to simultaneously emit any number of light beams from 3-D LIDAR system 100. Light reflected from objects in the environment is collected by collection optics 116. Collected light passes through collection optics 116 where it is focused onto each detecting element of the array of detecting elements 113. After passing through collection optics 116, the collected light is reflected from a mirror (not shown) onto each detector element.

In one aspect, a 3-D LIDAR device emits at least two beams of light into a three dimensional environment. Each beam of light is emitted from the 3-D LIDAR device at a different location. At least two of the emitted beams are projected from the 3-D LIDAR device such that the portion of the three dimensional environment illuminated by a first of the plurality of light beams substantially overlaps a portion of the three dimensional environment illuminated by a second of the plurality of light beams at a distance of at least five meters from the LIDAR device. In addition, the portion of the three dimensional environment illuminated by a first of the plurality of light beams does not substantially overlap a portion of the three dimensional environment illuminated by a second of the plurality of light beams at a distance of less than five meters from the LIDAR device.

The beams of light emitted from the 3-D LIDAR device are slightly divergent. In one example, the beam diameter is approximately 15 millimeters at the window of the device, and is approximately 20 centimeters at a distance of 100 meters from the device. Thus, the beam intensity is highest at the window of the device, and steadily decreases further away from the device. It follows that the risk of damage to the human eye is greatest in short range of the device and the risk diminishes as the distance from the device increases.

By emitting multiple beams of light from the 3-D LIDAR device at different locations, at short distances, the risk of eye damage is minimized because the beams are not overlapping. Hence, at short distances, only a single beam may incidentally interact with a human eye. As the distances increase, the beams begin to overlap, until a critical distance is reached where, ideally, two or more beams fully overlap with each other. In some examples, the critical distance is in a range of 100-200 meters away from the 3-D LIDAR device. In these distance ranges, more than one beam may incidentally interact with a human eye. However, at these distances, the combined beam intensity is below eye damage limits due to beam divergence.

Figure 3:
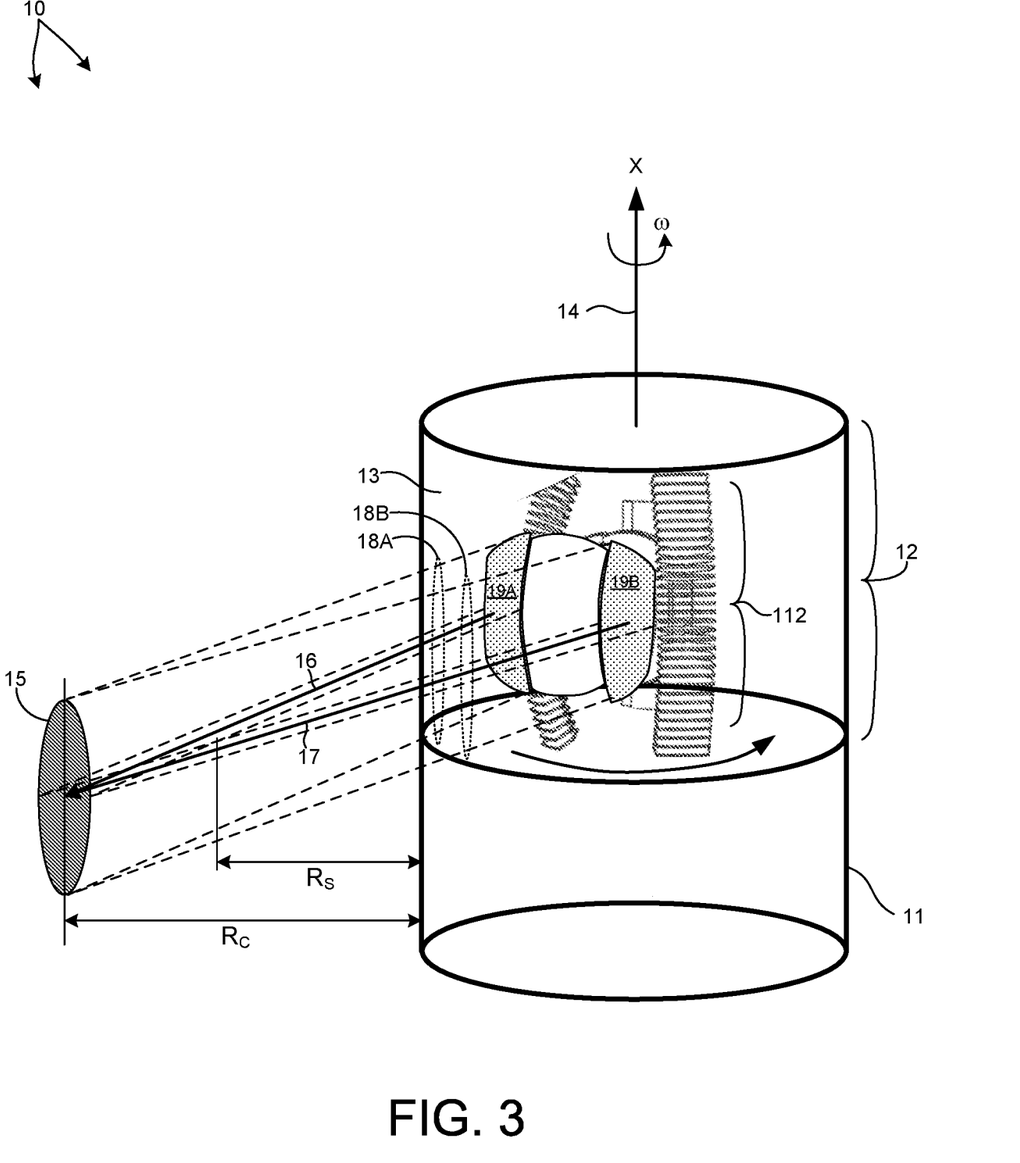
FIG. 3 is a simplified diagram illustrative of another embodiment of a 3-D LIDAR system 10 in at least one novel aspect.

FIG. 3 is a diagram illustrative of another embodiment of a 3-D LIDAR system 10 in one exemplary operational scenario. 3-D LIDAR system 10 includes a lower housing 11 and an upper housing 12 that includes a cylindrical shell element 13 (e.g., outer lens) constructed from a material that is transparent to infrared light (e.g., light having a wavelength within the spectral range of 700 to 1,700 nanometers). In one example, cylindrical shell element 13 is transparent to light having a wavelengths centered at 905 nanometers.

As depicted in FIG. 3, 3-D LIDAR system 10 includes a light emission/collection engine 112 tilted at a ninety degree angle with respect to central axis 14. In one aspect, two beams of light are emitted from 3-D LIDAR system 10 from different, spatially distinct locations of the 3-D LIDAR device. As depicted in FIG. 3, a beam of light characterized by chief ray 16 is emitted from light emission/collection engine 112 at the surface of illumination optic 19A and a beam of light characterized by chief ray 17 is simultaneously emitted from light emission/collection engine 112 at the surface of illumination optic 19B. The surfaces of illumination optics 19A and 19B are spatially distinct. In addition, the beam of light characterized by chief ray 16 is emitted from 3-D LIDAR system 10 at location 18A on the outer lens 13 and the beam of light characterized by chief ray 17 is simultaneously emitted from the 3-D LIDAR system 10 at location 18B on the outer lens 13. Location 18A and 18B are spatially distinct.

Furthermore, the beams are pointed such that they begin to overlap at a distance, $R_s$, from the device and maximally overlap at a critical distance, $R_c$, (e.g., 100-200 meters from 3-D LIDAR device 10). In the embodiment depicted in FIG. 3, the chief ray 16 of one illumination beam of light and the chief ray 17 of another illumination beam of light are illustrated. Each beam of light is projected outward into the surrounding environment along different trajectories. The trajectories intersect at location 15 in the far-field. Location 15 is located at a critical distance, $R_c$, from 3-D LIDAR system 10.

Each beam of light emitted from system 10 diverges slightly as illustrated in FIG. 3. In one example, a beam of light emitted from system 10 illuminates a spot size of 20 centimeters in diameter at a distance of 100 meters from system 10. In this manner, each beam of illumination light is a cone of illumination light emitted from system 10. For a portion of each beam trajectory from 3-D LIDAR system 10 to location 15, the beams do not intersect. At a distance, $R_s$, the beams begin to overlap. In some examples, the distance, $R_s$, where the beams begin to overlap is five meters, or more. Hence, at a distance of less than five meters, the beams do not overlap at all. As the distance increases beyond $R_s$, the percentage of overlap continues to increase until a maximum overlap is reached at the critical distance, $R_c$. Ideally, the percentage of overlap at the critical distance is 100%. However, in practice, any significant amount of overlap is beneficial as the overlapping illumination provides a stronger return signal to 3-D LIDAR device 10.

As depicted in FIG. 3, two beams of light are emitted from 3-D LIDAR system 10 from different locations of the 3-D LIDAR device and from two different lens elements. Furthermore, the beams are pointed such that they overlap at a critical distance from the device (e.g., 100-200 meters from 3-D LIDAR device 20). As depicted in FIG. 3, emission lens 19A and 19B are two different lens elements, each having their own optical axis. In some other embodiments, lens elements 19A and 19B may be constructed as a single optical component that includes two different lens elements, each having their own optical axis.

In the embodiment depicted in FIG. 3, 3-D LIDAR system 10 is configured to scan each of the plurality of beams of light 16 and 17 about central axis 14. As the beams of light rotate about central axis 14, each beam of light projected into the surrounding environment (e.g., each cone of illumination light associated with each beam) illuminates a volume of the environment corresponding the cone shaped illumination beam as it is swept around central axis 14. In general, any number of beams may be emitted from 3-D LIDAR system 10 to provide overlapping illumination in the far-field, or in different locations in the far-field.

In some embodiments, each beam configured to overlap with another beam in the far-field is generated by a separate illumination source (e.g., laser diode, LED, etc.) In some other embodiments, illumination light generated by a particular illumination source is subdivided and collimated to generate two or more different beams that are each directed such that they overlap in the far field.

Figure 4:
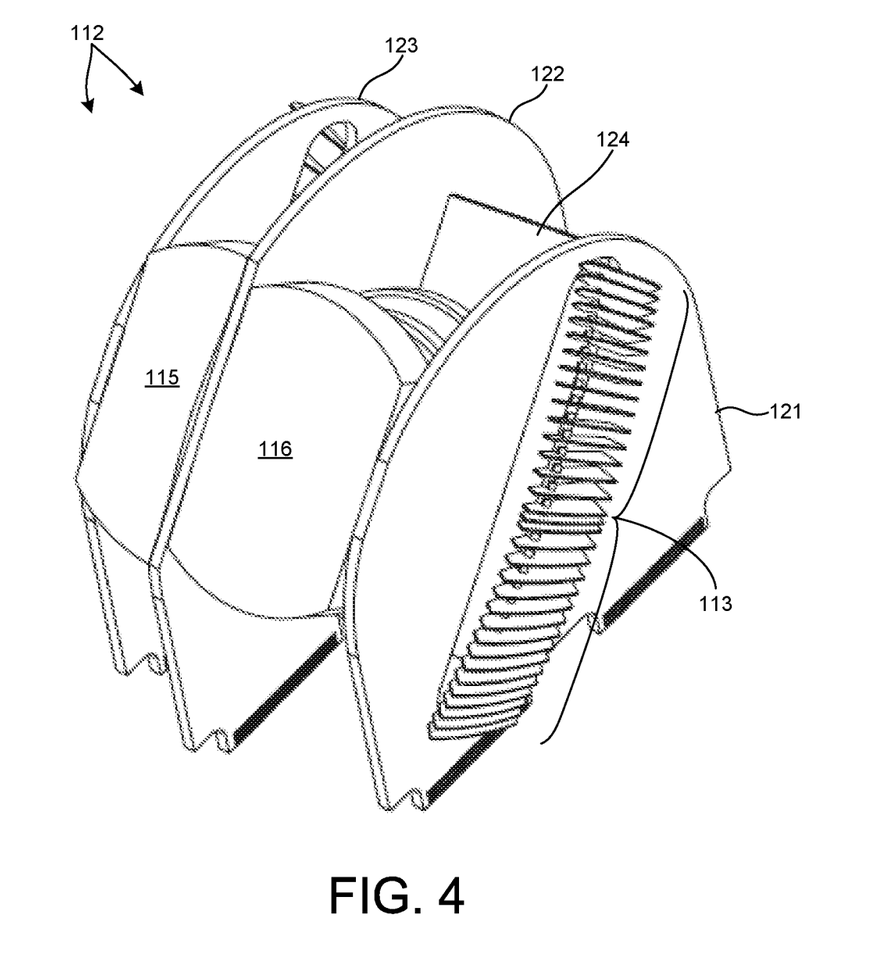
FIG. 4 depicts a view of light emission and collection engine 112 of 3-D LIDAR system 100.

FIG. 4 depicts another view of light emission/collection engine 112. In the depicted embodiment, light emission/collection engine 112 includes intermediate electronics boards 121, 122, and 123 which provide mechanical support and electrical connectivity between rotating electronics board 111 and various elements of light emission/collection engine 112. For example, each of the array of light detecting elements 113 is mounted to intermediate electronics board 121. Intermediate electronics board 121, in turn, is mechanically and electrically coupled to rotating electronics board 111. Similarly, each of the array of light emitting elements 114 is mounted to intermediate electronics board 123. Intermediate electronics board 123, in turn, is mechanically and electrically coupled to rotating electronics board 111. In another example, illumination optics 115 and collection optics 116 are mechanically mounted to intermediate electronics board 122. In this example, intermediate electronics board 122 spatially and optically separates the illumination optics 115 and the collection optics 116 to avoid contamination of the collected light with illumination light. Intermediate electronics board 122, in turn, is mechanically and electrically coupled to rotating electronics board 111. In this manner, the intermediate electronics boards provide mechanical and electrical connectivity and additional board area for mounting electrical components required for the operation of 3-D LIDAR system 100.

Figure 5:
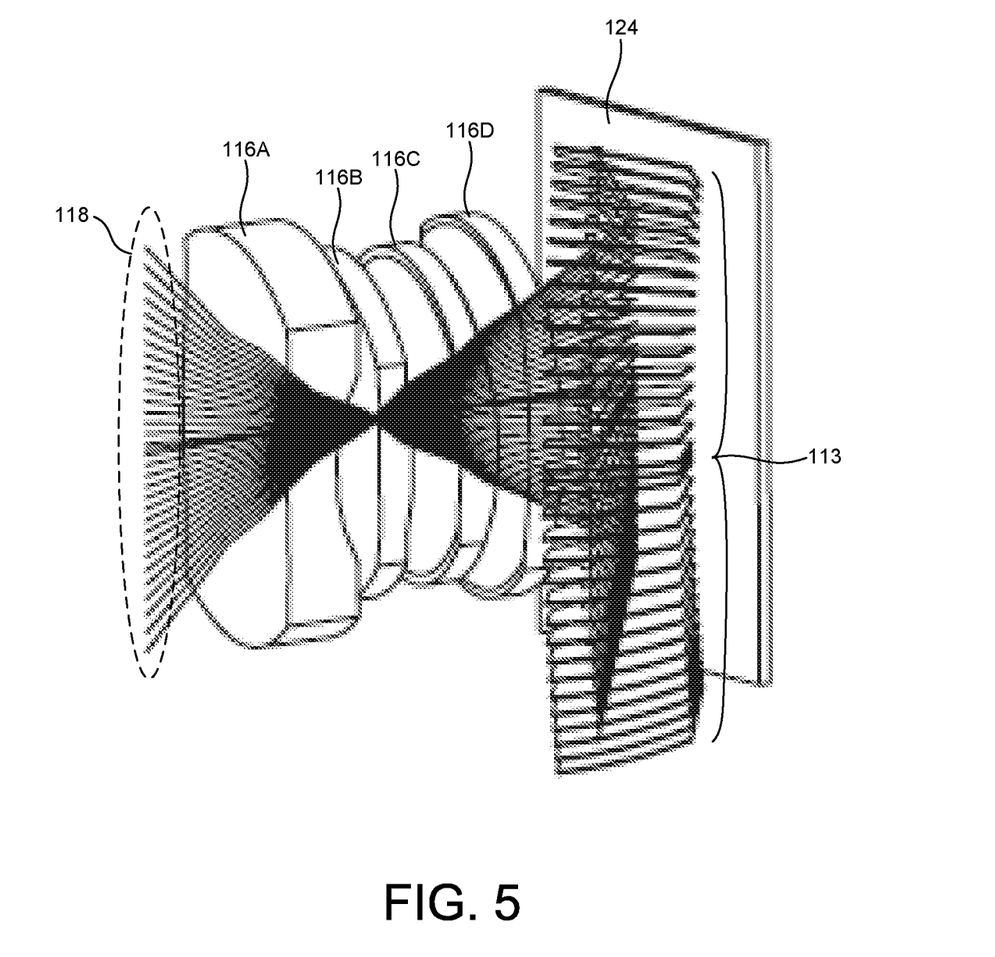
FIG. 5 depicts a view of collection optics 116 of 3-D LIDAR system 100 in greater detail.

FIG. 5 depicts a view of collection optics 116 in greater detail. As depicted in FIG. 5, collection optics 116 include four lens elements 116A-D arranged to focus collected light 118 onto each of the array of detecting elements 113. Light passing through collection optics 116 is reflected from mirror 124 and is directed onto each of the array of detecting elements 113. In another aspect, one or more of the optical elements of collection optics 116 is constructed from one or more materials that absorb light outside of a predetermined wavelength range that includes the wavelengths of light emitted by each of the array of light emitting elements 114. In one example, one or more of the lens elements are constructed from a plastic material that includes a colorant additive to absorb light having wavelengths less than infrared light generated by each of the array of light emitting elements 114. In one example, the colorant is Epolight 7276A available from Aako BV (The Netherlands). In general, any number of different colorants can be added to any of the plastic lens elements of collection optics 116 to filter out undesired spectra.

Figure 6:
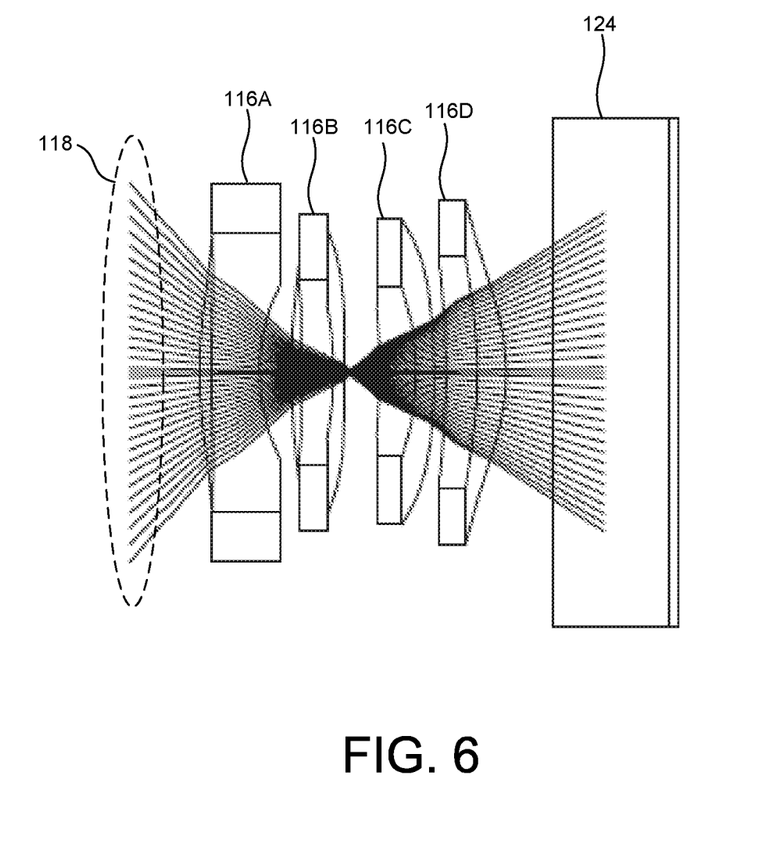
FIG. 6 depicts a cutaway view of collection optics 116 of 3-D LIDAR system 100 that illustrates the shaping of each beam of collected light 118.

FIG. 6 depicts a cutaway view of collection optics 116 to illustrate the shaping of each beam of collected light 118.

As described hereinbefore, one or more of the optical elements of collection optics 116 is constructed from one or more materials that absorb light outside of a predetermined wavelength range that includes the wavelengths of light emitted by each of the array of light emitting elements 114. However, in general, one or more of the optical elements of illumination optics 115 may also be constructed from one or more materials that absorb light outside of a predetermined wavelength range that includes the wavelengths of light emitted by each of the array of light emitting elements 114.

A LIDAR system, such as 3-D LIDAR system 10 depicted in FIG. 3, and system 100, depicted in FIG. 1, includes multiple, pulsed illumination sources emitting pulsed beams of illumination light from the LIDAR device into the surrounding environment. In some embodiments, the pulsed illumination sources are laser based. In some embodiments, the pulsed illumination sources are based on one or more light emitting diodes. In general, any suitable pulsed illumination source may be contemplated.

In one embodiment, two or more pulsed beams of illumination light simultaneously illuminate a particular location of the three dimensional environment (e.g., pixel) with pulses of illumination light. Light reflected from the location is detected by a photosensitive detector of the LIDAR system during a measurement window having a duration that is less than or equal to the time of flight of light from the LIDAR system out to the programmed range of the LIDAR system, and back. The photosensitive detector detects a return pulse or pulses of light reflected from a particular location of the three dimensional environment simultaneously illuminated by two or more illumination beams. In this manner, the reflection from a particular measurement location of each of the multiple illumination beams is captured by the LIDAR system.

In a further aspect, the LIDAR system determines the time of flight of the beams of illumination light from the LIDAR device to the particular spot of the three dimensional environment illuminated by the beams of illumination light and back to the LIDAR device. This determination is based on the reflected light detected during the measurement window. The distance between the LIDAR device and the particular location of the three dimensional environment illuminated by the beams of illumination light is determined based on the time of flight.

Figure 7:
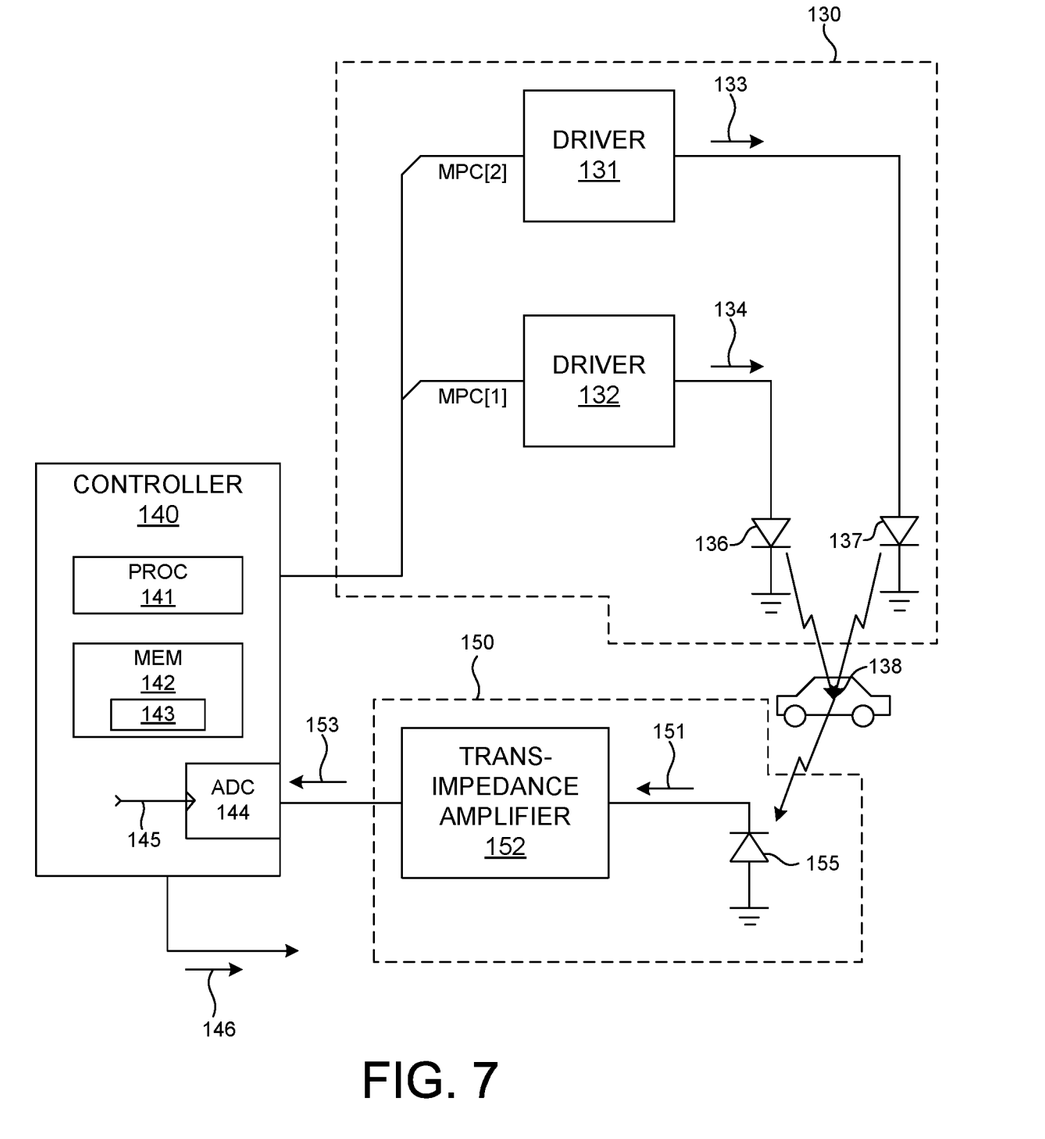
FIG. 7 depicts elements of a LIDAR system including a pulsed illumination system 130, a light detection system 150, and controller 140.

FIG. 7 depicts elements of a LIDAR system including a pulsed illumination system 130, a light detection system 150, and controller 140.

Pulsed illumination system 130 includes pulsed light emitting devices 136 and 137. Pulsed light emitting devices 136 and 137 generate simultaneous, pulsed light emission in response to pulsed electrical current signals 134 and 133, respectively. The light generated by pulsed light emitting devices 136 and 137 is focused and projected onto a particular location 138 in the surrounding environment by one or more optical elements of the LIDAR system. The beams of light generated by the pulsed lighting emitting devices 136 and 137 are directed such that they overlap at location 138. In one example, light emitted by pulsed light emitting devices 136 and 137 is focused and projected onto a particular location by illumination optics 115 that collimate the emitted light into pulsed beams of light 16 and 17 emitted from 3-D LIDAR system 10 as depicted in FIG. 3.

Pulsed illumination system 130 includes drivers 131 and 132 that supply current pulses to light emitting devices 137 and 136, respectively. The current pulses generated by drivers 131 and 132 are controlled by control signal, MPC. In this manner, the timing and shape of pulses generated by light emitting devices 136 and 137 are controlled by controller 140.

Figure 8:
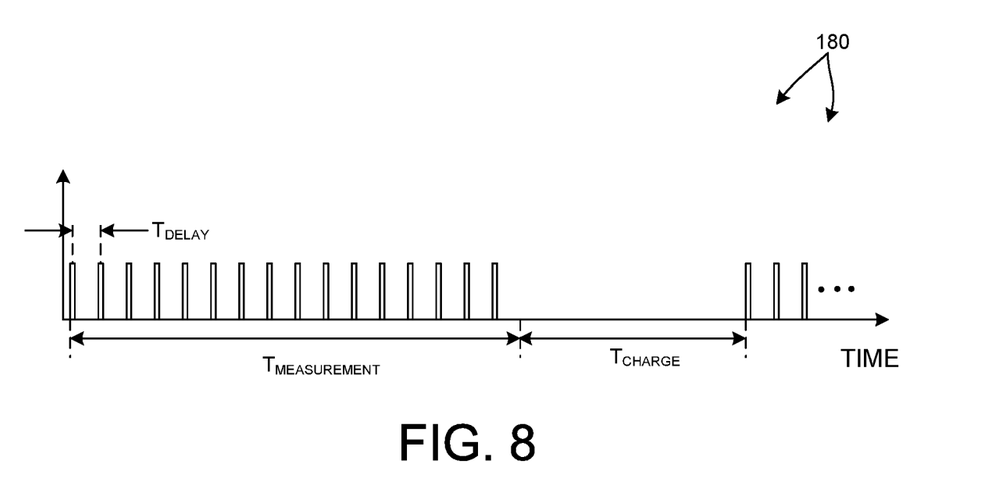
FIG. 8 depicts an exemplary diagram 180 illustrating the timing of light emission from each of sixteen different multiple beam illumination systems.

In a further embodiment, a LIDAR system, such as LIDAR system 100 depicted in FIG. 1, includes sixteen, multiple beam, pulsed illumination systems operating in coordination with a common controller (e.g., controller 140). FIG. 8 depicts an exemplary diagram 180 illustrating the timing of light emission from each of the sixteen, multiple beam illumination systems.

As depicted in FIG. 8, a measurement pulse is emitted from a first multiple beam illumination system. After a delay time, $T_{DELAY}$, a measurement pulse is emitted from a second multiple beam illumination system of the LIDAR device. In this manner a sequence of sixteen measurement pulses are emitted in different directions from the LIDAR device during a measurement period, $T_{MEASUREMENT}$. The drivers of each of the sixteen multiple beam illumination systems are charged after the measurement period for a charging period, $T_{CHARGE}$. After, the charging period, another measurement pulse is emitted from each multiple beam illumination system over a subsequent measurement period.

In some embodiments, the delay time is set to be greater than the time of flight of the measurement pulse to and from an object located at the maximum range of the LIDAR device. In this manner, there is no cross-talk among any of the sixteen multiple beam illumination systems.

In some other embodiments, a measurement pulse may be emitted from one multiple beam illumination system before a measurement pulse emitted from another multiple beam illumination system has had time to return to the LIDAR device. In some of these embodiments, care is taken to ensure that there is sufficient spatial separation between the areas of the surrounding environment interrogated by each set of beams to avoid cross-talk.

As depicted in FIG. 7, light reflected from location 138 simultaneously illuminated by multiple beams is detected by light detector 155. Light detector 155 generates an output signal 151 that is amplified by an analog trans-impedance amplifier 152. In general, the amplification of output signal 151 may include multiple, amplifier stages. In this sense, analog trans-impedance amplifier 152 is provided by way of non-limiting example, as many other analog signal amplification schemes may be contemplated within the scope of this patent document.

The amplified signal 153 is communicated to controller 140. An analog-to-digital converter (ADC) 144 of controller 140 is employed to convert the analog signal 153 into a digital signal used for further processing. Controller 140 generates an enable/disable signal 145 employed to control the timing of data acquisition by ADC 144 in concert with control signal, MPC.

Figure 9:
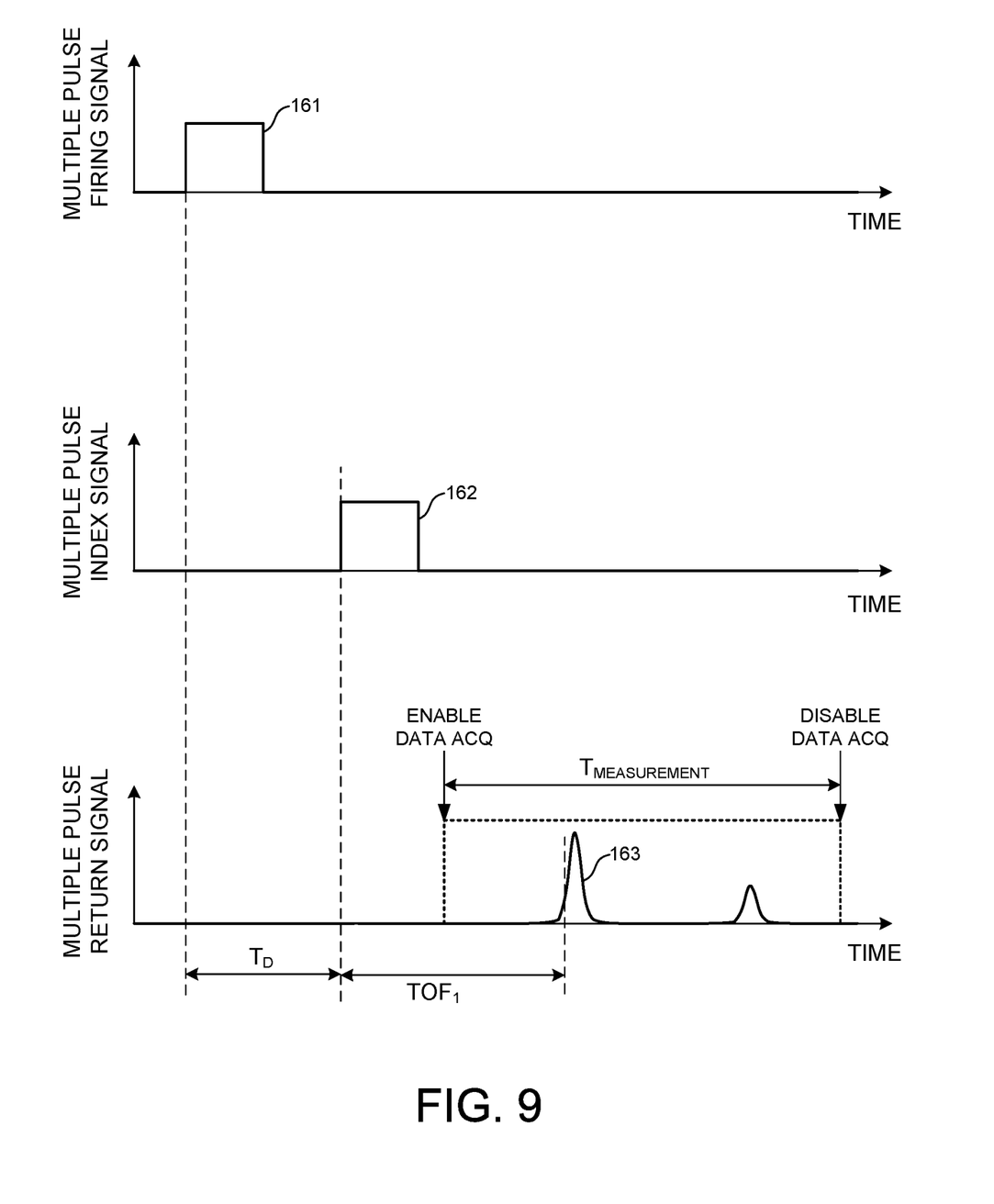
FIG. 9 depicts an illustration of the timing of emission of a pulse measurement beam and capture of the returning measurement pulse.

FIG. 9 depicts an illustration of the timing associated with the emission of a measurement pulse and capture of the returning measurement pulse sequence. As depicted in FIG. 9, the measurement begins with pulse firing signals 161 (e.g., MPC[1] and MPC[2]) generated by controller 140. Due to internal system delay, a pulse index signal 162 is determined that is shifted from the multiple pulse firing signal 161 by a time delay, $T_D$. The time delay includes the known delays associated with emitting light from the LIDAR system (e.g., signal communication delays and latency associated with the switching elements, energy storage elements, and pulsed light emitting device) and known delays associated with collecting light and generating signals indicative of the collected light (e.g., amplifier latency, analog-digital conversion delay, etc.).

As depicted in FIG. 9, a return signal 163 is detected by the LIDAR system in response to the illumination of a particular location by both light emitting devices 136 and 137. A measurement window (i.e., a period of time over which collected return signal data is associated with a particular measurement pulse) is initiated by enabling data acquisition from light detecting element 150. Controller 140 controls the timing of the measurement window to correspond with the window of time when a return signal is expected in response to the emission of the corresponding measurement pulse. In some examples, the measurement window is enabled at the point in time when the measurement pulse is emitted and is disabled at a time corresponding to the time of flight of light over a distance that is twice the range of the LIDAR system. In this manner, the measurement window is open to collect return light from objects adjacent to the LIDAR system (i.e., negligible time of flight) to objects that are located at the maximum range of the LIDAR system. In this manner, all other light that cannot possibly contribute to useful return signal is rejected.

As depicted in FIG. 9, return signal 163 includes two return measurement pulses that correspond with different objects in the path of the multiple beams. In general, signal detection is performed on all detected measurement pulses. Further signal analysis may be performed to identify the closest signal (i.e., first instance of the return measurement pulse), the strongest signal, and the furthest signal (i.e., last instance of the return measurement pulse in the measurement window). Any of these instances may be reported as potentially valid distance measurements by the LIDAR system. For example, a time of flight, $TOF_1$, may be calculated from the closest (i.e., earliest) return measurement pulse that corresponds with the emitted measurement pulse sequence as depicted in FIG. 9.

In the embodiment described with reference to FIG. 7, two different light emitting devices (i.e., light emitting devices 136 and 137) are employed to simultaneously generate two different beams directed to overlap in the far field. However, in general, a single light emitting device may be employed along with a beam splitting optic to subdivide the beam of light emitted from the single light emitting device into two or more beams that are directed to overlap in the far field by additional optical elements. In these embodiments, a single light emitting source simultaneously generates multiple beams that overlap in the far field with a single trigger signal, rather than having to coordinate the timing of multiple trigger signals (e.g., MPC[1] and MPC[2]) to achieve simultaneous overlapping illumination in the far field.

Figure 10:
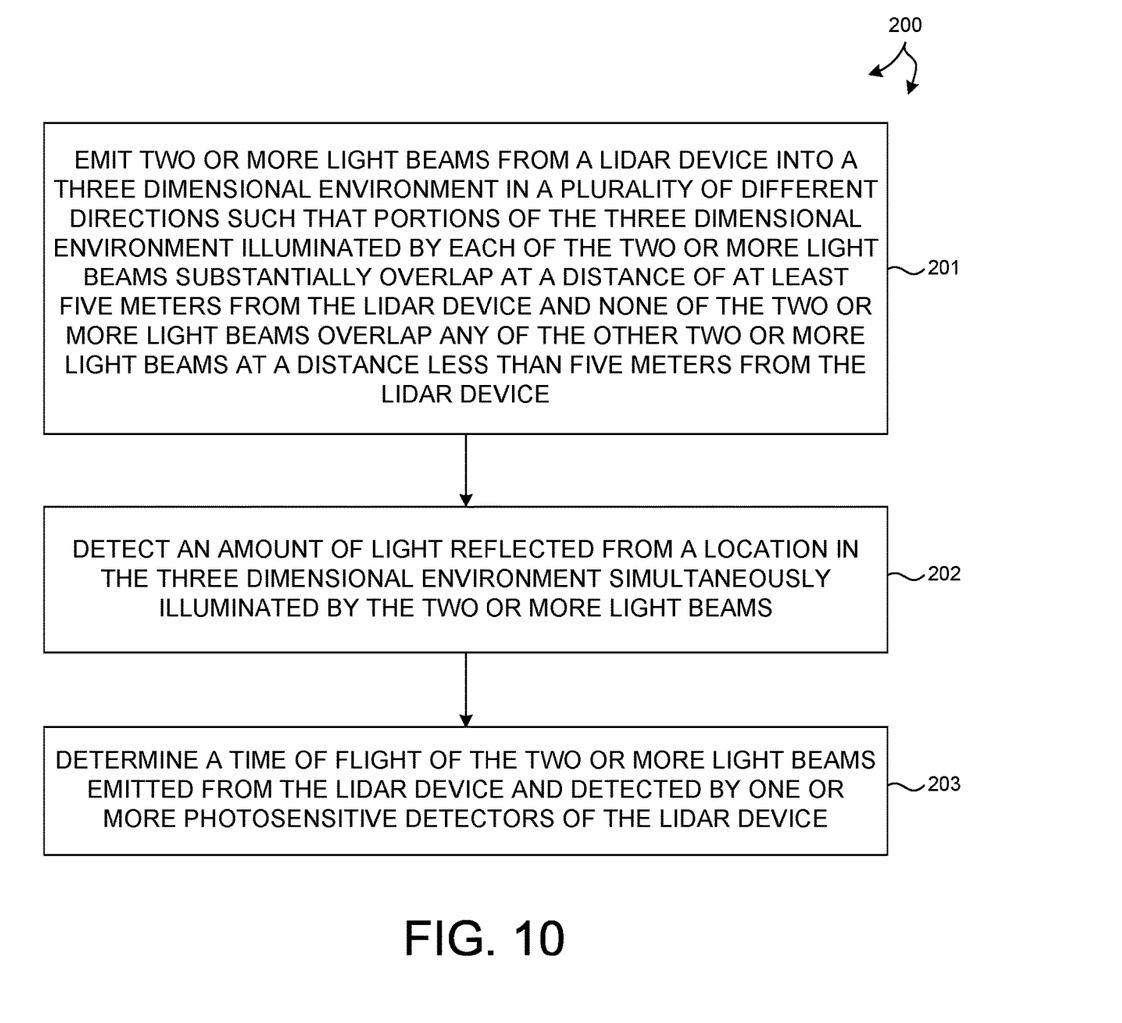
FIG. 10 depicts a flowchart illustrative of a method 200 of performing LIDAR measurements in at least one novel aspect.

FIG. 10 illustrates a method 200 of performing LIDAR measurements with multiple illumination beams overlapping in the far field in at least one novel aspect. Method 200 is suitable for implementation by any of the embodiments described herein. In one aspect, it is recognized that data processing blocks of method 200 may be carried out via a pre-programmed algorithm executed by one or more processors of controller 140, or any other general purpose computing system. It is recognized herein that the particular structural aspects of the described embodiments do not represent limitations and should be interpreted as illustrative only.

In block 201, two or more light beams are emitted from a LIDAR device into a three dimensional environment in a plurality of different directions. Portions of the three dimensional environment illuminated by each of the two or more light beams substantially overlap at a distance of at least five meters from the LIDAR device. None of the two or more light beams overlap any of the other two or more light beams at a distance less than five meters from the LIDAR device.

In block 202, an amount of light reflected from a location in the three dimensional environment simultaneously illuminated by the two or more light beams is detected.

In block 203, a time of flight of the two or more light beams emitted from the LIDAR device and detected by one or more photosensitive detectors of the LIDAR device is determined.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A light detection and ranging (LIDAR) device, comprising:
    a rotating board arranged perpendicular to an axis of rotation;
    a plurality of electronics boards each mounted to the rotating board;
    one or more illumination sources mechanically and electrically coupled to a first of the electronics boards and configured to emit two or more light beams each having a plurality of wavelengths centered at a same wavelength from the LIDAR device into a three dimensional environment in a plurality of different directions such that a portion of the three dimensional environment is illuminated by each of the two or more light beams, wherein a first of the two or more light beams is emitted from the LIDAR device at a first location, and a second of the two or more light beams is emitted from the LIDAR device at a second location that is spatially distinct from the first location;
    one or more photosensitive detectors mechanically and electrically coupled to a second of the electronics boards and configured to detect an amount of light reflected from a particular location in the three dimensional environment simultaneously illuminated by the two or more light beams;
    a third electronics board spatially and optically separating one or more illumination optics from one or more collection optics, wherein the one or more illumination optics and the one or more collection optics are respectively used to collimate the emitted light and the detected light; and
    a computing system configured to:
        determine a time of flight of the two or more light beams emitted from the one or more illumination sources and detected by the one or more photosensitive detectors; and
        determine a distance from the LIDAR device to the particular location in the three dimensional environment simultaneously illuminated by the two or more light beams based on the determined time of flight of the two or more light beams.

2. The LIDAR device of claim 1, wherein the portion of the three dimensional environment illuminated by each of the two or more light beams is located at least five meters from the LIDAR device and none of the two or more light beams overlap any of the other two or more light beams at a distance less than five meters from the LIDAR device.

3. The LIDAR device of claim 2, wherein the first and second locations are located on a surface of an optical element.

4. The LIDAR device of claim 2, wherein the first location is located on a surface of a first optical element and the second location is located on a surface of a second optical element.

5. The LIDAR device of claim 1, wherein the one or more illumination sources comprise:
    a light emitting device configured to emit a first amount of light, wherein the first amount of light is collimated into a first beam of light by the one or more illumination optics; and
    a beam splitting element configured to separate the first beam of light into a second beam of light and a third beam of light, wherein the second beam of light is emitted from the LIDAR device at the first location, and wherein the third beam of light is emitted from the LIDAR device at the second location that is spatially distinct from the first location, and wherein portions of the three dimensional environment illuminated by the second beam of light and the third beam of light substantially overlap at a distance of at least five meters from the LIDAR device and no portions of the second beam of light and the third beam of light overlap at any distance less than five meters from the LIDAR device.

6. The LIDAR device of claim 1, wherein a first of the one or more illumination sources emits a first of the two or more light beams from the LIDAR device at the first location, and a second of the one or more illumination sources emits a second of the two or more light beams from the LIDAR device at the second location, wherein the first and second locations are spatially distinct.

7. The LIDAR device of claim 1, wherein each of the one or more illumination sources is laser based or includes a light emitting diode.

8. The LIDAR device of claim 1, wherein each of the one or more illumination sources emits pulses of illumination light.

9. A light detection and ranging (LIDAR) device, comprising:
    a rotating board arranged perpendicular to an axis of rotation;
    a plurality of electronics boards each mounted to the rotating board;
    one or more light emitting devices mechanically and electrically coupled to a first of the electronics boards and configured to emit a first amount of light, wherein the first amount of light is collimated into a first beam of light;

a beam splitting element configured to separate the first beam of light into a second beam of light and a third beam of light each having a plurality of wavelengths centered at a same wavelength, wherein the second beam of light is emitted from the LIDAR device at a first location, and wherein the third beam of light is emitted from the LIDAR device at a second location that is spatially distinct from the first location, and wherein portions of the three dimensional environment illuminated by the second beam of light and the third beam of light substantially overlap at a distance of at least five meters from the LIDAR device and no portions of the second beam of light and the third beam of light overlap at any distance less than five meters from the LIDAR device;

one or more photosensitive detectors mechanically and electrically coupled to a second of the electronics boards and configured to detect an amount of light reflected from a particular location in the three dimensional environment simultaneously illuminated by the second and third beams of light;

a third electronics board spatially and optically separating one or more illumination optics from one or more collection optics, wherein the one or more illumination optics and the one or more collection optics are respectively used to collimate the emitted light and the detected light; and a computing system configured to:
  determine a time of flight of the second and third beams of light emitted from the one or more light emitting devices and detected by the one or more photosensitive detectors; and
  determine a distance from the LIDAR device to the particular location in the three dimensional environment simultaneously illuminated by the second and third light beams based on the determined time of flight of the second and third light beams.

10. The LIDAR device of claim 9, wherein the first and second locations are located on a surface of an optical element.

11. The LIDAR device of claim 9, wherein the first location is located on a surface of a first optical element and the second location is located on a surface of a second optical element.

12. The LIDAR device of claim 9, wherein each of the one or more light emitting devices is laser based or a light emitting diode.

13. A method comprising:
  emitting two or more light beams each having a plurality of wavelengths centered at a same wavelength from one or more illumination sources of a LIDAR device into a three dimensional environment in a plurality of different directions such that portions of the three dimensional environment illuminated by each of the two or more light beams substantially overlap at a distance of at least five meters from the LIDAR device and none of the two or more light beams overlap any of the other two or more light beams at a distance less than five meters from the LIDAR device, wherein the LIDAR device further comprises i) a rotating board arranged perpendicular to an axis of rotation, and ii) a plurality of electronics boards each mounted to the rotating board, and wherein the one or more illumination sources are mechanically and electrically coupled to a first of the electronics boards;
  detecting an amount of light reflected from a particular location in the three dimensional environment simultaneously illuminated by the two or more light beams;
  determining a time of flight of the two or more light beams emitted from the LIDAR device and detected by one or more photosensitive detectors of the LIDAR device,
  wherein the one or more photosensitive detectors are mechanically and electrically coupled to a second of the electronics boards,
  wherein the LIDAR device further comprises a third electronics board spatially and optically separating one or more illumination optics from one or more collection optics, the one or more illumination optics and the one or more collection optics being respectively used to collimate the emitted light and the detected light; and
  determining a distance from the LIDAR device to the particular location in the three dimensional environment simultaneously illuminated by the two or more light beams based on the determined time of flight of the two or more light beams.

14. The method of claim 13, wherein a first of the two or more light beams is emitted from the LIDAR device at a first location, and a second of the two or more light beams is emitted from the LIDAR device at a second location that is spatially distinct from the first location.

15. The method of claim 14, wherein the first and second locations are located on a surface of an optical element.

16. The method of claim 14, wherein the first location is located on a surface of a first optical element and the second location is located on a surface of a second optical element.

17. The method of claim 14, further comprising:
  emitting a first amount of light from one or more light emitting devices;
  collimating the first amount of light into a first beam of light; and
  splitting the first beam of light into a second beam of light and a third beam of light, wherein the second beam of light is emitted from the LIDAR device at the first location, and wherein the third beam of light is emitted from the LIDAR device at the second location that is spatially distinct from the first location, and wherein portions of the three dimensional environment illuminated by the second beam of light and the third beam of light substantially overlap at a distance of at least five meters from the LIDAR device and no portions of the second beam of light and the third beam of light overlap at any distance less than five meters from the LIDAR device.

18. The LIDAR device of claim 1, wherein none of the two or more light beams overlap with each other within a first threshold distance from the LIDAR device, wherein the two or more light beams begin to overlap with each other at or outside the first threshold distance, and wherein the two or more light beams maximally overlap at or outside a second threshold distance from the LIDAR device, the second threshold distance further from the LIDAR device than the first threshold distance.

19. The LIDAR device of claim 18, wherein the first threshold distance and second threshold distance are set based on a determined risk of damage to a human eye due to simultaneous exposure to the two or more light beams.

20. The LIDAR device of claim 18, wherein the first threshold distance is 5 meters and wherein the second threshold distance is 100-200 meters.

21. The LIDAR device of claim 1, wherein the plurality of electronics boards are each directly mounted to the rotating board, and the one or more illumination optics and the one or more collection optics are mechanically coupled to the third electronics board.

22. The LIDAR device of claim 9, wherein the plurality of electronics boards are each directly mounted to the rotating board, and the one or more illumination optics and the one or more collection optics are mechanically coupled to the third electronics board.

23. The method of claim 13, wherein the plurality of electronics boards are each directly mounted to the rotating board, and the one or more illumination optics and the one or more collection optics are mechanically coupled to the third electronics board.

\* \* \* \* \*